United States Patent [19]

Fowler, III et al.

[11] Patent Number: 5,197,879

[45] Date of Patent: Mar. 30, 1993

[54] ORTHODONTIC, MEDICAL, DENTAL TOOL

[76] Inventors: Hudson D. Fowler, III, Battles Rd., Gates Mills, Ohio 44040; Robert E. Cherry, 8732 E. Field Ct., Pickerington, Ohio 43147; William E. Flasche, 2618 Glenchester, Wexford, Pa. 15090; Russell J. Logan, 2870 Chatham, Pepper Pike, Ohio 44124; Gary Worner, 8211 West Hill Dr., Chagrin Falls, Ohio 44020

[21] Appl. No.: 756,326

[22] Filed: Sep. 6, 1991

[51] Int. Cl.[5] .................. A61C 3/14; A61C 3/16; B25B 7/06
[52] U.S. Cl. ...................... 433/159; 433/4; 81/416
[58] Field of Search ............... 433/146, 157, 159, 160, 433/4; 81/416, 417

[56] References Cited

U.S. PATENT DOCUMENTS

| 168,012 | 9/1875 | Gaillard | 433/146 |
|---|---|---|---|
| 1,475,569 | 11/1923 | Dondero | 81/416 |
| 2,611,288 | 9/1953 | Schiffbauer | 81/416 |
| 2,632,661 | 3/1953 | Cristofv | 81/416 |
| 3,581,400 | 6/1971 | Snead | 433/4 |

FOREIGN PATENT DOCUMENTS 424344 2/1935 United Kingdom ............... 433/159

Primary Examiner—Gene Mancene
Assistant Examiner—Cindy A. Cherichetti
Attorney, Agent, or Firm—Renner, Otto, Boisselle & Sklar

[57] ABSTRACT

A separable hinged orthodontic, dental tool that includes a pair of scissor halves, each half having a handle portion, a nose portion and a substantially identical hinge portion, each hinge portion including at least one female mating section and one male mating section for engagement with a corresponding male and female mating section, respectively, on the other scissor half.

12 Claims, 2 Drawing Sheets

ORTHODONTIC, MEDICAL, DENTAL TOOL

FIELD OF THE INVENTION

The present invention relates generally to a tool, and, more particularly, to a orthodontic, medical, dental tool (tool) having hinged separable elements facilitating effective sterilization of the tool.

BACKGROUND OF THE INVENTION

With the increasing public awareness and concern over the spread of diseases, such as Acquired Immune Deficiency Syndrome (AIDS) or hepatitis strains, the effective sterilization of orthodontic, medical, and dental tools is becoming more important. A common method of sterilizing tools is by washing and then placing the tool in an autoclave and/or dry heat oven where the tool is heated to approximately 375° F. for a period of time in an effort to kill bacteria and viruses contained thereon. However, some tools contain hidden surfaces which can protect bacteria, etc., harbored therein from the complete sterilization effects of the autoclave. Exemplary tools exhibiting this problem are those having hinged parts, such as plier-like or scissor-like orthodontic tools, where access to the interior regions of the hinge is not readily provided.

When scissor-like tools are sterilized the bacteria harbored in the hinge assembly may not be subject to adequate heat to be destroyed. Additionally, over repeated sterilizations, the bacteria, etc., both alive and dead, tend to build up in the hinge assembly, thus causing it to corrode, to bind up, and/or to become more difficult to operate. Consequently, the hinge may then be oiled. However, the oil can compound the sterilization problem by trapping additional bacteria within the hinge.

While medical tools having a separable hinge, thus allowing separation of the tool for sterilization purposes, have been developed, these tools have not succeeded in practice for a number of reasons. Some of these separable hinged tools separate too easily, thus causing the problem of unwanted separation in some circumstances. Other tools are difficult to disassemble, such as those requiring removal of a screw. Further, other tools have too much "play" between the hinged sections thus rendering them unsuitable for many applications.

It would be desirable to provide a tool allowing for easy disassembly, cleaning and effective sterilization while still providing an accurate and sturdy tool.

SUMMARY OF THE INVENTION

The present invention provides a scissor-like medical tool with separable hinged elements. Each element contains at least one male and female dovetail section for mating engagement with the corresponding sections of the other element. The tool stays assembled over a large, e.g., 90%, range of movement, while still providing ease of disassembly at the maximum open position. The dovetail mating engagement hinge further provides a sturdy and accurate tool allowing use in many applications, since there is little or no play between the assembled elements.

In accordance with the invention a separable hinged tool includes a pair of scissor halves, each scissor half having a handle portion, a nose portion and a substantially identical hinge portion, each hinge portion including at least one female mating section and one male mating section for engagement with a corresponding male and female mating section, respectively, on the other scissor half.

These and other objects, advantages, features and aspects of the present invention will become apparent as the following description proceeds.

To the accomplishments of the foregoing and related ends, the invention, then comprises the features hereinafter fully described in the specification and particularly pointed out in the claims, the following description and the annexed drawings setting forth in detail a certain illustrative embodiment of the invention, this being indicative, however, of but one of the various ways in which the principals of the invention may be employed. It will be appreciated that the scope of the invention is to be determined by the claims and the equivalents thereof.

DETAILED DESCRIPTION OF THE INVENTION

Figure 1:
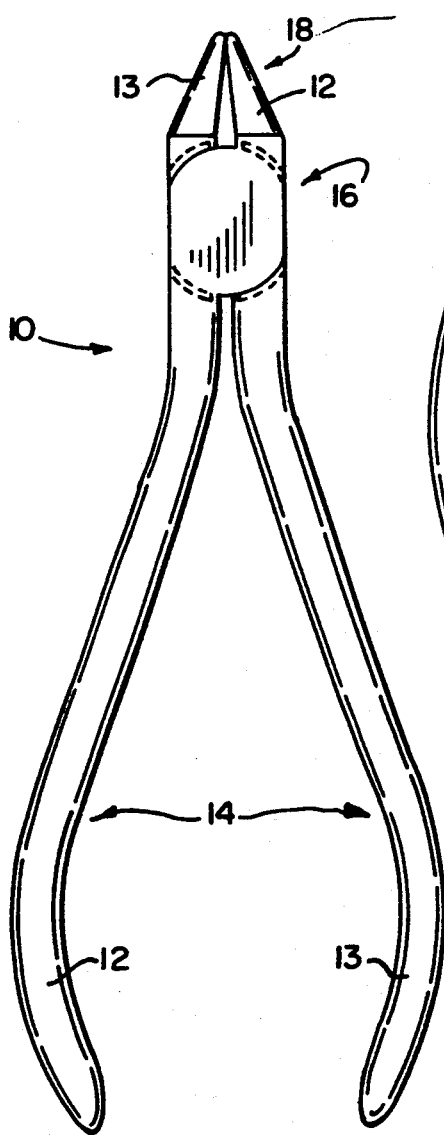
FIG. 1 is an illustration of a scissor-like medical tool in accordance with the present invention.

With reference to the several figures in which like reference numerals depict like items, and initially to FIG. 1, there is shown a tool 10 in accordance with the present invention. The tool 10 includes two substantially identical scissor halves 12 and 13. Each half 12, 13 includes a handle section 14, a hinge section 16, and a nose section 18. While the nose section 18 illustrated in the figures corresponds to a pair of bird beak pliers, it will be appreciated readily that other types of nose sections 18 may be used, such as to provide a cutting tool or a three-jaw pair of pliers, all of such modifications being within the scope of the present invention.

Figure 6:
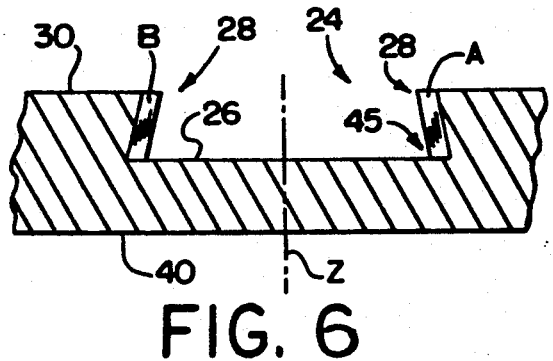
FIG. 6 is a sectional view of the hinge area of FIG. 5 taken along the line 6—6 showing the female dovetail section of the hinge.
Figure 7:
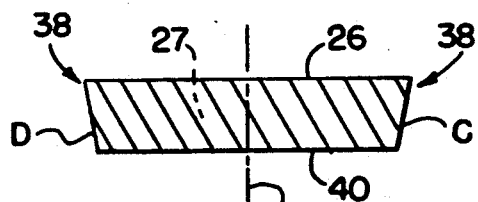
FIG. 7 is a generalized sectional view of the hinge area of FIG. 5 taken along the line 7—7 illustrating the male dovetail section of the hinge.
Figure 8:
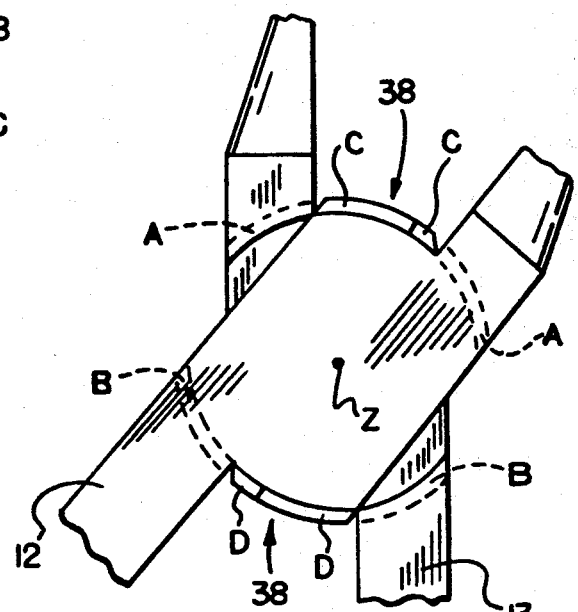
FIG. 8 is a partial view of the tool in an extreme open position prior to disassembly.

Referring now to FIGS. 2 through 8 it is noted that this scissor half 12 is substantially identical to the scissor half 13. Consequently, while much of the following discussion describes only one scissor half, for example scissor half 12, the discussion applies equally to the other scissor half. With both scissor halves 12 and 13 oriented as shown in FIG. 8, assemblage of the halves to form the tool 10 simply requires that the be fitted together in the extreme open position and then rotated slightly towards the closed position to engage. When engaged, the scissor halves 12, 13 rotate relative to one another about the point or axis Z which extends through the center of the hinge section 16. Consequently, when engaged, movement of the handles 14 towards each other causes the nose sections 18 likewise to move towards each other as the direction of movement and force is translated about the axis Z. Similarly, movement of the handles 14 apart from each other moves the nose sections 18 apart.

Figure 3:
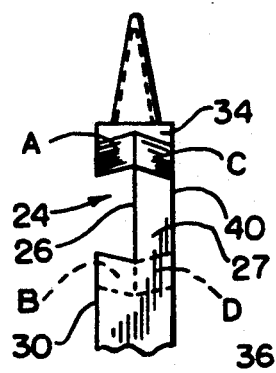
FIG. 3 is a partial side view of the scissor half of FIG. 2 seen from the line 3—3 thereof.
Figure 4:
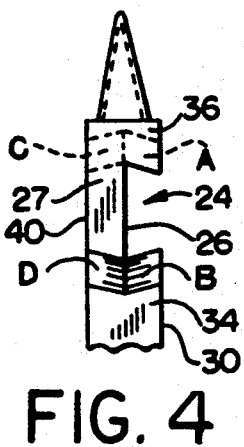
FIG. 4 is a partial side view of the scissor half of FIG. 2 seen from the line 4—4 thereof.

The hinge area 16 has an essentially circular inner periphery 20 from which extends the mating dovetail sections, which will be described later. The lateral portions of the circular inner periphery 20 are truncated to form flat sides 22. The hinge area 16 of the scissor half 12 includes a recess 24, as seen in FIGS. 3 and 4, extending in depth half of the width of the hinge section to form a flat inner surface 26. The recess 24 extends radially from the hinge center Z to the boundaries formed by the circular periphery 20 and flat sides 22 of the hinge 16 and is adapted for engagement with the hinge area 16 of the mating scissor half 13. When the scissor halves 12, 13 are engaged, the recesses 24 in each scissor half will accommodate the solid portion 27 of the hinge area 16 adjacent the recess so that the two mated scissor halves will have a width of one scissor half in the hinge area.

Figure 2:
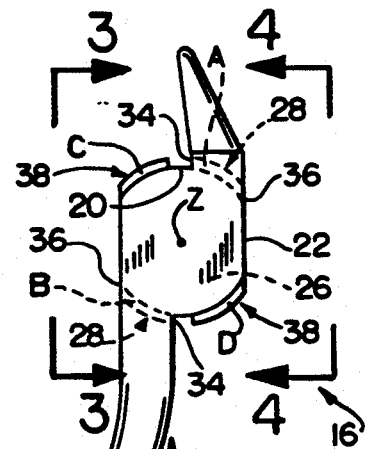
FIG. 2 is a plane view of one-half of the tool illustrated in FIG. 1.
Figure 5:
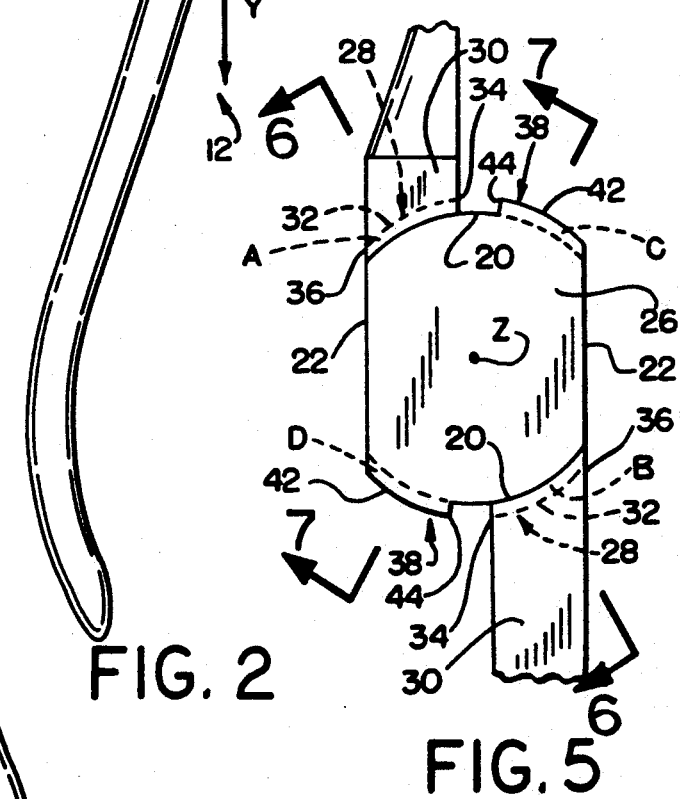
FIG. 5 is an enlarged view of the hinge section of a scissor half flipped over from the position of FIG. 2.

With specific reference now to FIG. 5 there is shown a close up of the hinge area 16 of a scissor half, such as that of the scissor half 12 rotated 180° around the axis Y shown in FIG. 2, or the scissor half 13 oriented for engagement with the scissor half 12. Extending radially outwardly from the recess 24 in the areas where the circular periphery 20 adjoins the handle section 14 and nose section 18 are diametrically opposed arcuate female dovetail slots 28. The arcuate female dovetail slots 28 extend from the outer surface 30 of the plier body at the boundary of the circular periphery 20 axially inwardly at a radially outwardly projecting 10° angle and terminate in the plane of the flat inner surface 26. The arcuate female dovetail slots 28 thus cut into the handle section 14 or nose section 18 along an arc 32 lying in the plane of the flat surface 26 and running from an interior side 34 of the corresponding section 14, 18 to an exterior side 36 of that section adjoining a flat side of the hinge area 16. As can be seen from FIG. 6, which is a sectional view of the hinge area 16 of the scissor half taken along the cut 6—6 shown in FIG. 5 which extends through the female dovetail sections 28, as well as from FIGS. 3 and 4, the diametrically opposed female dovetail sections 28 form opposed inclined arcuate mating surfaces A, B suitable for radially and axially securing corresponding mating surfaces C, D of diametrically opposed male dovetail portions 38 of a mating scissor half.

Also extending outwardly from the circular periphery 20 of the hinge section 16 are diametrically opposed male arcuate dovetail protrusions 38 for engagement with the corresponding female dovetail slots 28 in the other scissor half. The male arcuate dovetail protrusions 38 extend axially inwardly from an outer surface 40 of the plier body 12 at the circular periphery 20 and radially outwardly at a 10° angle terminating in the plane of the flat inner surface 26. The male dovetail protrusions 38 thus protrude from the inner circular periphery 20 to form arcs 42 which run from a point 44 near a handle or nose section 14, 18 towards a flat side 22. A cross-section taken along the cut 7—7 through the axis Z of the hinge area 16 intersecting the male dovetail portions 36 is shown in FIG. 7. The inclined external arcuate mating surfaces C, D of the diametrically opposed male dovetail sections 36 form a structure adapted to fit within the arcuate mating surfaces A, B, respectively, of the diametrically opposed female dovetail slots 28, as shown in cross-section in FIG. 6. As is seen in FIG. 7 the width of the hinge 16 in the area from which the male dovetail sections protrude is one-half the width of the plier body. For reference, the bottom surface 40 corresponds to the outer face 40 of the hinge 16 and the top surface 26 corresponds to the bottom of the recess 24, or the flat inner hinge surface 26, as shown in FIGS. 3 and 4.

When the scissor halves 12, 13 are mated, the flat inner hinge surfaces 26 will come to lie adjacent each other. The male dovetail sections 38, such as that seen in FIG. 7, of one scissor half will be rotated 180 degrees in the plane of the paper, to become situated for engagement in the female dovetail sections 28, as seen in FIG. 6, of another scissor half, or vice-versa. FIG. 8 shows two scissor halves 12, 13 in an extreme open position with one half rotated 180° around its long axis Y. In the extreme open position the male dovetail protrusions lie outside and adjacent the corresponding female dovetail section 28, thus permitting disengagement of the scissor halves such as for sterilization purposes. Rotating the scissor half 12 around the axis Z relative to the scissor half 13 in the counterclockwise direction will cause each male dovetail protrusion 38 to enter the corresponding female dovetail slot 28. As the scissor half 12 is further rotated counterclockwise, the male dovetail protrusions 38 will enter the female dovetail slots 28 and the mating surfaces C, D and A, B of the male and female dovetail sections, respectively, will engage. Movement of the scissor halves 12, 13 will thus be constrained to rotation about the Z axis only. This hinge design significantly reduces the non-rotational rigidity, or slop, of the tool of the present invention over conventional separable tools.

Appropriate angles for the mating surfaces C, D and A, B of the male and female dovetail sections 38, 28, respectively, have been found to be approximately 10°, as noted above. Increasing the angle increases the surface area of mating surfaces A, B and C, D of the female and male dovetail sections 28, 38 respectively, and thus may improves the non-rotational rigidity. However, the increased angle also complicates machining and reduces the internal angle 45 of the female dovetail slot 28. Excessively reducing this internal angle 45 can make cleaning and disinfecting of the tool somewhat more difficult.

Figure 9:
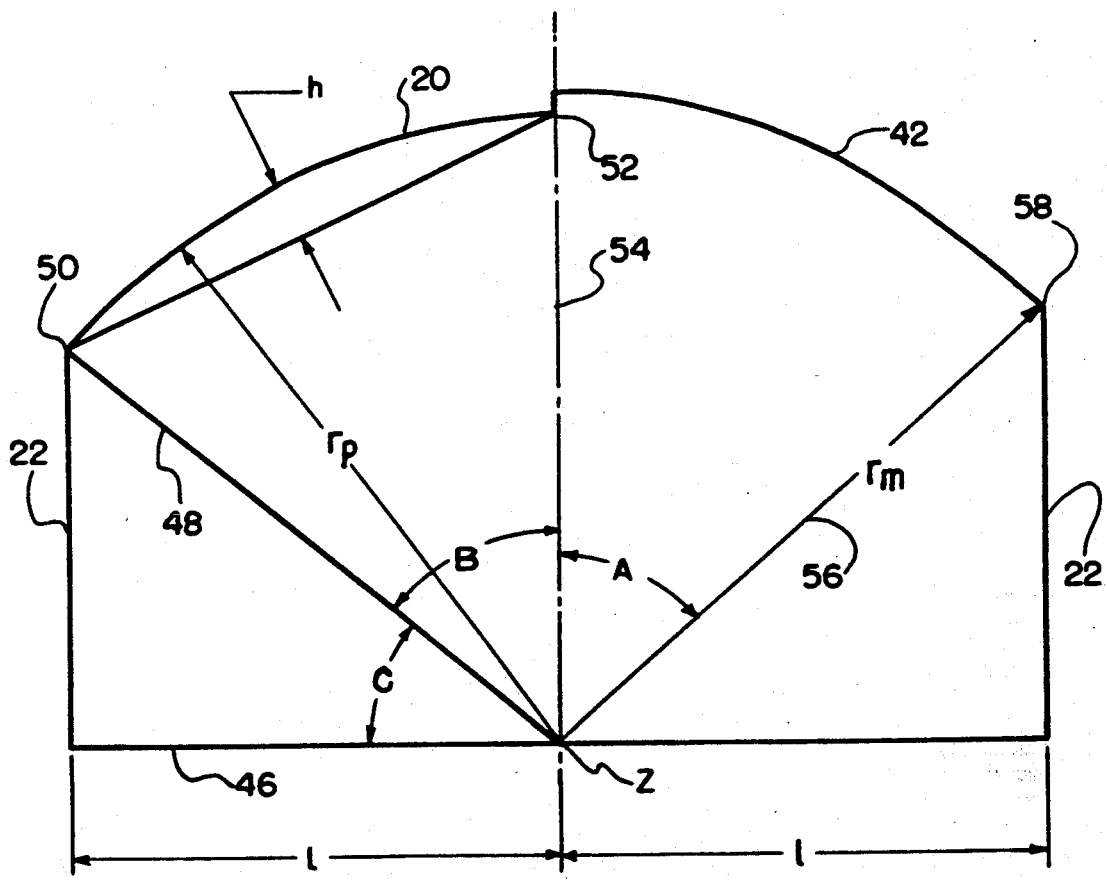
FIG. 9 is a schematic diagram of certain hinge dimensions allowing the tool to be easily assembled and separable.

Referring now to FIG. 9, there is seen a schematic illustration of the dimensions of the hinge permitting easy separation of the scissor halves while promoting effective securement when in use. The radius of the circular periphery 20 of the inner hinge region 16 is labelled as "$r_p$", while the distance to the outer radius 42 of the male dovetail protrusion is labelled as "$r_m$". "C" denotes the angle from a line 46 extending from axis Z perpendicular to the flat side 22 to a line 48 extending from the axis Z to the intersection 50 of the flat side and the circular periphery 20. The maximum distance between the circular periphery 20 and a chord running from the intersection 50 of the periphery with the flat side 22 and the intersection 52 of the circular periphery with a line 54 extending from the axis Z parallel to the flat sides 22 is denoted as "h". The angle "B" represents the angle between the line 48 and the line 54. The angle "A" represents the angle between the line 54 and a line 56 extending from axis Z to the intersection 58 of the arc 42 struck from axis Z with a radius of $r_m$ with a flat side 22. The angle A is also the angle at which the individual scissor halves 12, 13 will become separable. Finally, each dimension "l" represents one-half of the distance between the flat sides 22 of the hinge 16.

In order for the scissor halves to be assembled, the male dovetail protrusions 38 must clear the female dovetail slots 28 when the pliers are in the extreme open position. To meet this condition the dimension "l" must satisfy the following relationship:

$$l \leq r_p - h \qquad (1)$$

However, it is desirable that the scissor halves 12, 13 disassemble only when the scissor halves are in an extreme open position. This occurs when the dimension l is maximized according to:

$$l = r_p - h \qquad (2)$$

It is apparent that as the dimension l increases, so will the arcuate length of the female and male dovetail sections 28, 38, respectively, increase. Acceptable values for $r_p$ and h must thus be determined to provide the dimension l. The chord to arc distance h can be expressed as:

$$h = r_p(1 - \cos(B/2)) \qquad (3)$$

Angle B can be expressed in terms of the angle C as:

$$B = 90° - C \qquad (4)$$

where angle C is defined by the relation:

$$l/r_p = \cos(C) \qquad (5)$$

The angle A is given by:

$$l/r_m = \sin(A) \qquad (6)$$

Solutions to these equations are obtained iteratively by selecting a suitable disengagement angle A and a value for $r_p$. Recalling that $r_m$ equals $r_p$ plus the protrusion distance of the male dovetail, which is known, the values for l and h are defined through the equations above. The value for $r_p$ is varied until both definitions of angle C, given in equations 4 and 5 above are satisfied. Angle A is then varied until a satisfactory set of l's and $r_p$'s are generated. The hinge geometry is thus defined within these constraints. For the specific embodiment of the orthodontic pliers described herein, a suitable value for $r_p$ has been found to be approximately 0.3 inches and a suitable value for the disengagement angle A has been found to be approximately 53°.

The tolerance for fitting the scissor halves together are provided through the actual hinge design. Note that since there is a small clearance provided between the male and female dovetail portions 38, 28, such as is indicated at 60 in FIG. 4, the angle B does not actually extend to the line 54 (FIG. 9) as the model above assumes. Thus the actual value for h will be slightly smaller than that yielded through the equations above. Consequently, while a maximum value for l was obtained through the equation:

$$l = r_p - h$$

the value yielded was slightly less than the true maximum, thus providing a slight but adequate clearance for plier assembly.

Preferably the scissor halves are constructed of 440C stainless steel. The plier bodies may be manufactured by investment casting the 440C stainless steel and then machining the casting to the appropriate finished dimensions. Machining may be jig grinding, Electro-static Discharge Milling (EDM), or Computer Numerical Controlled milling (CNC). It has been found that EDM machines the male dovetails and other areas of close tolerances very accurately. For some applications, such as a plier-like cutting tool, it may be desirable to heat treat the machined part to a greater hardness, such as RC 60. It may also be desirable in such an embodiment to employ carbide cutting tips. The machined part is then buffed and polished and subjected to a passivation step, if desired, to remove free iron from the surface of the part and to reduce the potential for oxidation over repeated sterilizations.

What is claimed is:

1. A separable hinged orthodontic, medical or dental tool, comprising a pair of scissor halves, each scissor half having a handle portion, a nose portion and a substantially identical pinless hinge portion without any central axial projections or mating recesses; said hinge portion including at least one planar, solid female mating section and at least one male mating section for engagement with a corresponding male and female mating section, respectively, on the other scissor half, said at least one female mating section being a female dovetail slot, and said at least one male mating section being a male dovetail protrusion.

2. The tool of claim 1, wherein said male dovetail protrusion and said female dovetail slot include mating faces oriented at approximately 10° axial direction of the hinge portion.

3. The tool of claim 2, wherein said scissor halves are separable when opened to an angle of approximately 53° and non-separable when opened to an angle of less than approximately 53°.

4. The tool of claim 1, wherein said nose portions include a cutting surface.

5. The tool of claim 1, wherein said nose portions include gripping surfaces.

6. The tool of claim 1, wherein said at least one female mating section is two female mating sections and said at least one male mating section is two male mating sections.

7. The tool of claim 6, wherein said two female mating sections are diametrically opposed from each other and said two male mating sections are diametrically opposed from each other.

8. The tool of claim 7, wherein said one of said two female mating sections extends into said handle portion and the other of said two female mating sections extend into said nose portion.

9. The tool of claim 8, wherein said two female mating sections and said two male mating sections are arcuate and concentric.

10. The tool of claim 9, wherein ½ the width of the hinge protion of each scissor half is approximately equal to the radius of the arcuate male mating sections minus the maximum distance between a chord extending between the ends of an arcuate male mating section and the most distal portion of such arcuate male mating section.

11. The tool of claim 1, wherein said at least one female mating section and said at least one male mating section are arcuate.

12. The tool of claim 1, wherein said of least one female mating section and said at least one male mating section are concentric.

* * * * *